(12) United States Patent
Zamar

(10) Patent No.: US 9,918,895 B2
(45) Date of Patent: Mar. 20, 2018

(54) STIMULATION APPARATUS

(71) Applicant: Auris Medical Limited, Eastbourne (GB)

(72) Inventor: Antonios Camille Zamar, Eastbourne (GB)

(73) Assignee: AURIS MEDICAL LIMITED, Eastbourne, East Sussex (GB)

( * ) Notice: Subject to any disclaimer, the term of this patent is extended or adjusted under 35 U.S.C. 154(b) by 0 days.

(21) Appl. No.: 15/216,281

(22) Filed: Jul. 21, 2016

(65) Prior Publication Data

US 2016/0324718 A1    Nov. 10, 2016

Related U.S. Application Data

(63) Continuation of application No. 14/643,393, filed on Mar. 10, 2015, now abandoned, which is a
(Continued)

(30) Foreign Application Priority Data

Sep. 9, 2008    (GB) .................................. 0816448.5

(51) Int. Cl.
*A61F 5/00* (2006.01)
*A61H 19/00* (2006.01)
(Continued)

(52) U.S. Cl.
CPC ............. *A61H 19/32* (2013.01); *A61H 19/30* (2013.01); *A61H 19/34* (2013.01); *A61H 19/40* (2013.01);
(Continued)

(58) Field of Classification Search
CPC ..... A61H 19/00; A61F 5/41; A61F 2005/411; A61F 2005/414; A61F 2005/417; A61F 2005/418
(Continued)

(56) References Cited

U.S. PATENT DOCUMENTS 6,338,721 B1    1/2002  Lebecque ........................ 601/71
6,416,461 B1 *  7/2002  Zamar ........................ A61F 5/41
                                                            600/39
(Continued)

FOREIGN PATENT DOCUMENTS

DE    29807440 U1    8/1998
DE    20311823 U1    9/2003
(Continued)

OTHER PUBLICATIONS

Office Communication in U.S. Appl. No. 13/062,705, filed Mar. 23, 2011 dated Sep. 12, 2013.
(Continued)

*Primary Examiner* — Samuel Gilbert
(74) *Attorney, Agent, or Firm* — Licata & Tyrrell P.C.

(57) ABSTRACT

Apparatus and methods for use of apparatus for applying targeted stimulation at or adjacent the base of the area of the glans of the penis, wherein the apparatus comprises a contact portion having a first contact surface conforming substantially to the longitudinal profile of the penis, the contact portion further having a second contact surface, raised, in use, inwardly of the first contact surface towards the penis, to project in use into positive engagement with the area at or adjacent the base of the glans of the penis are provided.

12 Claims, 3 Drawing Sheets

Related U.S. Application Data continuation of application No. 13/062,705, filed as application No. PCT/GB2009/051117 on Mar. 9, 2009, now Pat. No. 8,998,795.

(51) Int. Cl.
*A61H 23/00* (2006.01)
*A61H 23/02* (2006.01)
*A61H 23/04* (2006.01)

(52) U.S. Cl.
CPC ............ *A61H 19/50* (2013.01); *A61H 23/00* (2013.01); *A61H 23/02* (2013.01); *A61H 23/04* (2013.01); *A61H 2201/165* (2013.01)

(58) Field of Classification Search
USPC .............................. 600/38–41; 128/897, 898
See application file for complete search history.

(56) References Cited

U.S. PATENT DOCUMENTS

| | | | |
|---|---|---|---|
| 8,998,795 B2* | 4/2015 | Zamar | ........................ A61F 5/41 600/38 |
| 2006/0178602 A1 | 8/2006 | Teng et al. | ........................ 601/70 |
| 2009/0012355 A1* | 1/2009 | Lin | ........................ A61H 19/34 600/41 |
| 2009/0105529 A1 | 4/2009 | Crarer | ........................ 600/38 |

FOREIGN PATENT DOCUMENTS

| | | |
|---|---|---|
| EP | 1049433 B1 | 1/2004 |
| WO | WO 98/44852 | 10/1998 |
| WO | WO 99/36008 | 7/1999 |
| WO | WO 08/031160 | 3/2008 |

OTHER PUBLICATIONS

Office Communication in U.S. Appl. No. 13/062,705, filed Mar. 23, 2011 dated Mar. 6, 2014.
Office Communication in U.S. Appl. No. 13/062,705, filed Mar. 23, 2011 dated Dec. 10, 2015.
International Search Report in PCT/GB2009/051117 dated Apr. 26, 2010.
International Preliminary Examination Report in PCT/GB2009/051117 dated Jan. 24, 2011.
Office Communication in U.S. Appl. No. 14/643,393, filed Mar. 10, 2015 dated Apr. 23, 2015.
Office Communication in U.S. Appl. No. 14/643,393, filed Mar. 10, 2015 dated Jan. 22, 2016.

* cited by examiner

STIMULATION APPARATUS

This patent application is a continuation of U.S. patent application Ser. No. 14/643,393, filed Mar. 10, 2015, which is a continuation of U.S. application Ser. No. 13/062,705, filed Mar. 23, 2011, which is the U.S. National Stage Application of International Application No. PCT/GB2009/051117, filed Sep. 3, 2009, which claims the benefit of priority from Great Britain Application No. 0816448.5, filed Sep. 9, 2008, teachings of each of which are herein incorporated by reference in their entirety.

The present invention relates to apparatus for stimulating body parts, in particular the penis.

In this regard, the applicant of the present invention has previously disclosed apparatus of this sort in EP1049433. In EP1049433, the applicant identified a method of alleviating the problems associated with premature ejaculation, this method involving the targeted stimulation of the penis to an extent whereby it becomes desensitized and tolerized to other stimulants that may lead to ejaculation. As a result, the latency period to ejaculation can be delayed.

The apparatus put forward in EP1049433 concerned a penile ring which included a substantially triangular section that, when in position, extended in the axial direction of the penis and contacted the ventral area of the penis at the base of the glans, to thereby apply a stimulating action in order thereby to provide the overall desensitising effect. This has been proven through reviewed medical research studies to delay ejaculation on average 11 fold in 61% compared to 3 fold in 40% with the cognitive behaviour therapy in sufferers of premature ejaculation.

The applicant has now sought to improve the stimulation effect on which his invention is based.

In a first aspect of the present invention there is provided apparatus for applying targeted stimulation to the area at or adjacent the base of the glans of the penis, wherein the apparatus comprises:—a contact portion having a first contact surface conforming substantially to the longitudinal profile of the penis, the contact portion further having a second contact surface, raised, in use, inwardly of the first contact surface towards the penis, to thereby project in use into positive engagement with the area at or adjacent the base of the glans of the penis.

In this connection, the applicant has devised an improved apparatus, which enhances the stimulating effect, which is integral to his desensitizing method. When the apparatus is held against the penis, the first contact surface positions and aligns the apparatus into position, whilst the second contact surface, being provided inwardly of the first contact surface affords enhanced contact at the area at the base of the glans of the penis.

Preferably, the second contact surface has an arcuate profile, for example a domed configuration. This provides a 3-dimensional stimulation surface for acting on the targeted area of the penis.

Conveniently, the first and/or second contact surface has a plurality of protrusions, which are preferably configured to extend substantially orthogonally therefrom. Such protrusions can intensify the stimulation effect provided by the apparatus.

The contact portion may further comprise side wings which extend substantially circumferentially from either side of the raised second contact surface for contact, in use, at or adjacent the underside of the corona of the penis. In this way, a greater surface is enclosed by the apparatus and a greater surface area of the penis is acted upon by the apparatus. The side wings may be provided with a plurality of excitation protrusions.

Preferably, the contact portion is formed as part of an open channel, which, in use, can be held against the underside of the penis. Such a channel shape is particularly suited to facilitating a reciprocating longitudinal action on the penis. The first contact surface in this regard is profiled to house and align the apparatus readily on a user's penis.

Conveniently, the side wings are provided on the inner surface of the channel. The channel in this respect provides a suitable support surface for the side wings.

The raised second contact surface may be malleable. It may have a moderate degree of hardness for exerting pressure, but be sufficiently soft such that it can conform to the profile of the penis where they inter engage, whilst not injuring the skin of the penis. In this connection, the whole apparatus may be malleable or of moderate hardness. The contact surfaces may have, in this respect, a defined profile for targeting stimulation to specific areas on the penis, but the contact surfaces may be malleable to an extent to accommodate differences in penis profile.

Preferably, the apparatus accommodates a vibrator for vibrating the first and/or second contact surface, or the entire channel. A vibrator of suitable frequency can act to optimize the stimulating effect of the apparatus.

The apparatus may further comprise excitation means for setting up a moving ridge in the contact portion. The excitation means may in this connection comprise mechanical and/or fluid oscillation means for generating a suitable wave profile in the contact portion.

According to a further aspect of the present invention, there is provided apparatus for applying targeted stimulation to the area at or adjacent the base of the glans of the penis comprising: a contact portion having a contact surface provided with one or more stimulating protrusions, the contact surface being arranged to form a substantially open channel which, in use, contacts around at least the undersurface of the glans. Such an open channel or sleeve provides a suitable support for the components of the apparatus.

Preferably, a leading edge of the contact surface has an inclined profile to follow the contour of the glans. Such a profile affords enhanced contact with the penis.

Conveniently, the apparatus further comprises a channel shaped body, the contact portion being formed on an inside surface of the body. Such an open channel or sleeve provides an apparatus that is readily usable, providing a support for the components of the apparatus whilst being readily held and manipulated.

According to a further aspect of the present invention there is provided a method of tolerizing a penis by stimulation for delaying the latency period to ejaculation, the method comprising the steps:—a) utilizing the apparatus of any preceding claim on a regular basis, by stroking the apparatus either manually or through the aforementioned vibrator or excitation means against the base of the glans and/or adjacent area up to the point of feeling the urge to ejaculation; b) discontinuing the stroking for a pause; and c) restarting stroking again; wherein the process is repeated for up to 30 minutes or until the "point of no return". This is known as the "Start-Stop technique".

Preferably, the apparatus is used for a period of up to 30 minutes at least once a week for up to six weeks. Through medical research studies, it has been found that the apparatus may optimally be used period of up to 30 minutes three times a week for up to six weeks.

According to a further aspect of the present invention there is provided apparatus for concurrently stimulating male and female partners, the apparatus comprising a first contact portion directed inwardly towards the penis for applying targeted stimulation at or adjacent the base of the area of the glans of the penis, the apparatus further comprising a second outwardly directed contact portion for applying stimulation to a female's genitalia. The device can be used as a sex toy to stimulate the male during foreplay or the male and female during penetrative sex when in a ring configuration.

Preferably, the first and/or second contact portions each have respective contact surfaces having undulating configurations. The contact surfaces may be formed of or with ridges, dimples, protrusions and/or grooves.

In a preferred embodiment, the first and second contact surfaces facing the underside surface of the user's penis may together form a complex curved surface. The complex curved surface may take the form of a first concave curve defining a longitudinal channel for accommodating the penis, in combination with a second convex curve forming a hump running transversely across the channel.

The complex curve may take the form of a hyperbolic paraboloid, namely a saddle configuration.

The apparatus may have side portions depending from the contact surface, which may comprise recessed portions for affording holding areas for a user of the apparatus. More preferably, the recessed areas together define a flange for engagement by a thumb and finger of a user in order to assist grip of the apparatus in one hand.

In preferred embodiments, the complex curve is provided with protrusions for optimising the massaging and stimulating effect of the apparatus.

The recessed areas on the side portions of the apparatus may further have incorporated therein a switch for operating a vibrator or excitation means provided in the apparatus.

The apparatus may include a ring or an interrupted ring for holding the apparatus in position.

In preferred embodiments, the second contact surface is formed to have the contours of a hemisphere or raised triangle.

Examples of the present invention will now be described with reference to the accompanying drawings, in which.

As shown in FIGS. 1 to 4, there is shown apparatus 1 for stimulating the penis 2. The apparatus comprises a contact portion having an open channel or sleeve like member 3, formed from a substantially half cylinder section. Such a channel like member will conform generally to the shape of the underside of the main body of the penis, particularly when erect or semi-erect. The contact portion is, in this regard, profiled to house and align the apparatus readily on a user's penis. This simplifies ensuring the apparatus is placed and held in the correct place during operation.

Figure 1:
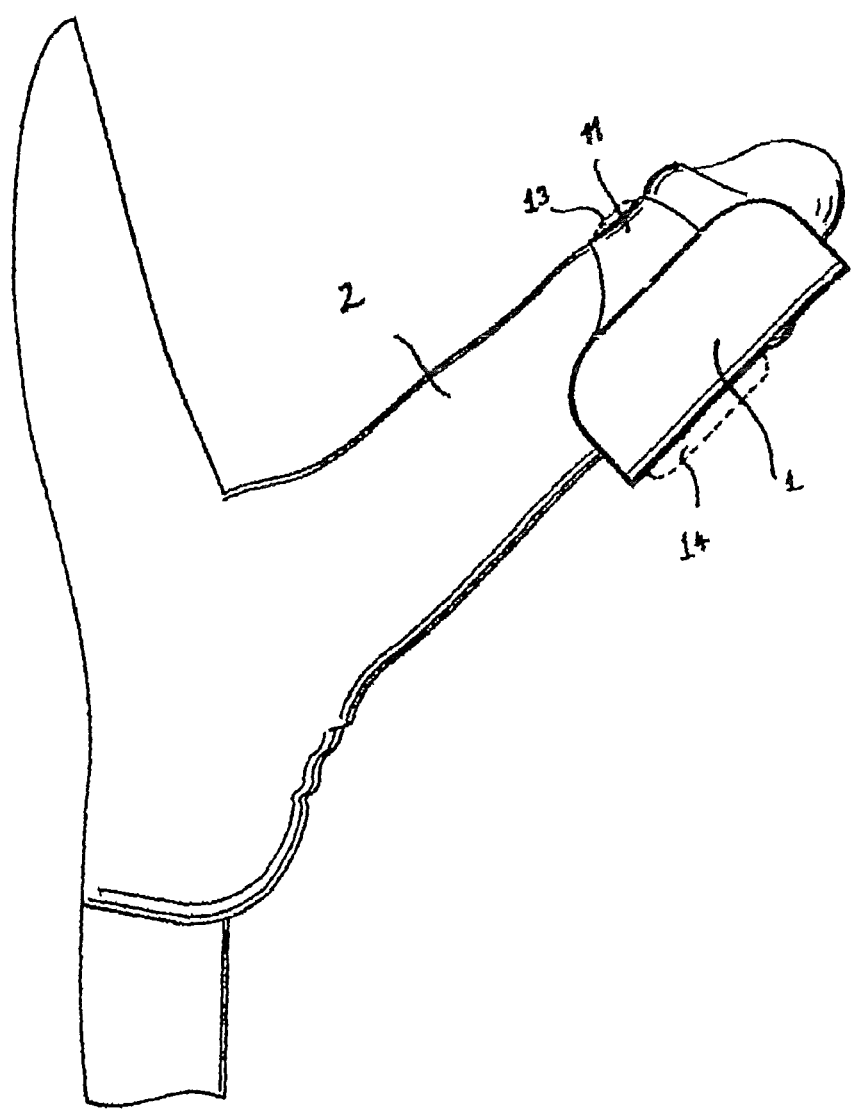
FIG. 1 is a side view of the apparatus in place on a penis.

On an inner surface of the channel like member there is provided a raised portion in the form of a dome 4. This is positioned towards an upper end of the channel-like member and centrally there within. The dome extends inwardly of the channel-like member, namely inwardly of the profile of the underside of the main body of the penis. The contact portion of the apparatus hence presents a first contact surface, namely conforming to the general profile of the channel-like member, which with the apparatus in place at or adjacent the glans, is aligned substantially with the axial direction of the penis as shown in FIG. 1. The dome 4 provides a second contact surface which deviates from this general profile, and with the apparatus in place, the dome positively engages with the area at the base of the glans 5 of the penis. As a result of the second contact surface being raised relative to the first contact surface, when the first contact surface is urged into position on the penis, the second contact surface has enhanced positive contact with the glans.

Figure 2:
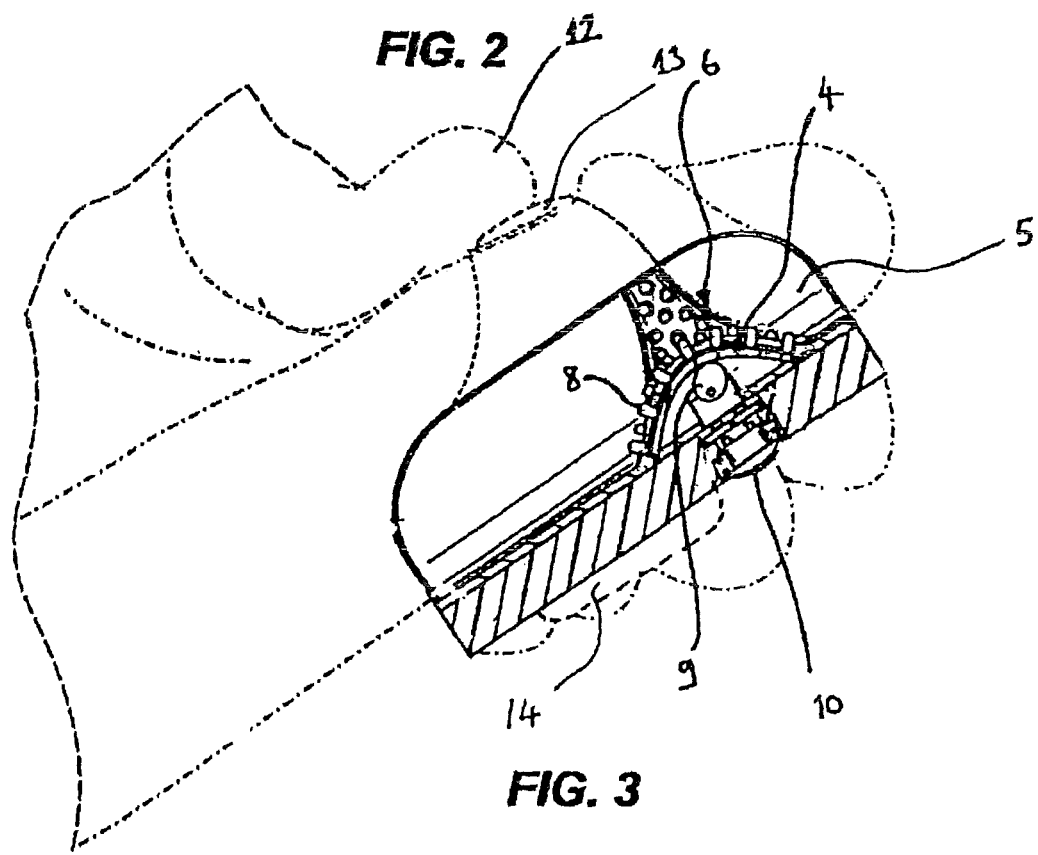
FIG. 2 shows the apparatus of FIG. 1 in part cross-section in use.

As a result of its three-dimensional profile, the dome significantly increases and thereby enhances the contact area with the penis at the base of the glans. Indeed, the dome promotes contact also with the corona 6 on the underside of the penis as shown in FIG. 2. This enhanced contact augments the stimulating and hence desensitizing effect of the apparatus.

Figure 3:
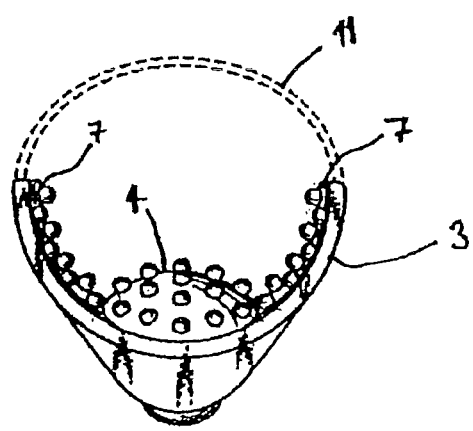
FIG. 3 shows an end view of the apparatus.
Figure 4:
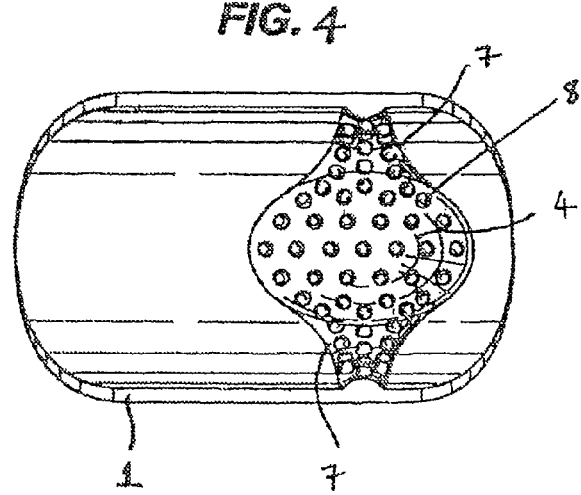
FIG. 4 shows a plan view from above of the apparatus.

FIGS. 3 and 4 show side wings 7 provided at the channel-like member. These side wings further promote the contact with the penis, particularly around the underside of the corona. As shown, the wings are contoured to extend around to match the profile of the corona, to thereby optimize the contact at this area of the penis.

The apparatus is shown provided in the context of a channel or sleeve like member as this affords a suitable body for housing the contact surfaces and for ease of manipulation by a user 12. The channel in this respect provides a length of first contact surface facilitating an axial reciprocation of the apparatus along the length of the penis.

However, other configurations are possible, for example, with the dome 4 and wings 7 being provided on an interrupted band or ring member. The apparatus may for example include a supporting band 11 for retaining it in position hence forming a ring.

The contact surfaces are shown provided with protrusions 8 which project orthogonally therefrom. These enhance the stimulating effect of the apparatus. The protrusions may be provided in any suitable form, for example, ridges, dimples, or grooves.

A vibrating means 9 can be provided within the dome, as shown in FIG. 2. This can be operated though switch 10. The vibrating means may provide different vibration patterns to suit the user's requirements. One such pattern may allow for an axial reciprocation of the contact surface according to a range of vibrating speeds or a designated wave pattern, which creates the dome effects in an otherwise flat or smaller dome configuration.

Moreover, provided the material is suitable, the apparatus can be used for penetrative vaginal sex. In this respect, the channel member 3 and band 11 would have a reduced thickness to allow such penetration.

The channel member 3 and/or the band 11 may moreover be provided with stimulating protrusions, such as ridges, dimples or grooves on their outer facing surfaces such that the female may benefit from a stimulating effect the same time as the male. In other words, during foreplay the pair may lie in the missionary position with the man's penis resting on the female's genitalia, such that the outer surface of the underside of the channel member 3 can, for example, provide a stimulating effect on the clitoris. Alternatively, during penetrative vaginal sex, protrusions on the outer surface of the ring may be arranged to be in contact with the female genitalia. Such stimulating protrusions can be provided as part of raised surfaces on the channel member and/or the band, as shown as elements 13 and 14 in phantom lines in FIGS. 1 and 2. These elements may have arcuate profiles, for example domed shaped, and be driven to vibrate to provide enhanced stimulation.

The present invention hence concerns apparatus for stimulating a penis to the extent that it becomes desensitized and tolerized, thereby delaying the latency period to ejaculation and hence may also be used for sufferers of premature ejaculation.

The present invention encapsulates a method of desensitizing a penis, using the apparatus, the method comprising using the apparatus on a repeated basis, to thereby tolerize the penis to stimulation. In this regard, in order to benefit from the tolerizing effect of the apparatus it should be used preferably 3 times a week for up to six weeks for no longer than 30 minutes following the principles of start-stop technique outlined above. In the method, the apparatus is held against the underneath of the penis and the penis is then stoked therewith.

Figure 5:
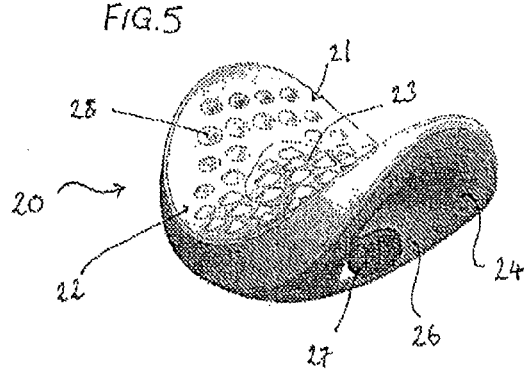
FIG. 5 shows a perspective view of a further embodiment of the invention.
Figure 6:
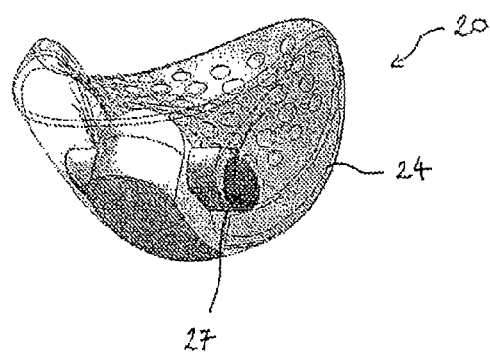
FIG. 6 shows a perspective and partly outlined view from below of the embodiment of FIG. 5.

FIGS. 5 and 6 show a further embodiment of the present invention. In this embodiment, the apparatus takes the form of a relatively compact unit 20, whose upper penis-facing surface 21 takes the form of a complex curved surface. The complex curved surface has a first concave curve defining a channel 22 for accommodating a length of a user's penis, at or adjacent the glans, in combination with a second convex curve forming a hump 23 running transversely across the channel. The channel again acts to assist in the correct original positioning and holding of the apparatus on a user's penis. The hump 23 is configured to engage positively with at least the undersurface of the glans. The complex curve is in effect "saddle-shaped" or a hyperbolic paraboloid.

The unit has side portions 24 depending from the contact portion, which have opposed recessed portions 26 for affording holding areas for a user of the apparatus. The holding areas are configured to receiving the thumb and a finger of a user. A switch 27 for operating a vibration means is provided within the recessed area.

The complex curved surface is moreover provided with protrusions such as ridges or dimples 28, in order to enhance the stimulation effect of the unit.

What is claimed is:

1. Apparatus for applying targeted stimulation at or adjacent a base of an area of a glans of a penis, wherein the apparatus comprises:—a contact portion having a first contact surface conforming to a longitudinal profile of the penis, the contact portion further having a second contact surface, said second contact surface raised inwardly of the first contact surface towards the penis, to project into positive engagement with the area at or adjacent the base of the glans of the penis, wherein the contact portion is formed as an open channel from a half cylinder section, which can be held against an underside of a corona of the penis, the inner surface of the channel being formed by side wings that extend circumferentially from either side of the raised second contact surface for contact on and around the underside of the corona of the penis.

2. Apparatus according to claim 1, wherein the first and/or second contact surface has a plurality of protrusions.

3. Apparatus according to claim 1, wherein the side wings are provided with a plurality of excitation protrusions.

4. Apparatus according to claim 1, wherein the apparatus accommodates a vibrator for vibrating the first and/or second contact surface.

5. Apparatus according to claim 1, further comprising excitation means for setting up a moving ridge in the contact portion forming the second contact portion.

6. Apparatus according to claim 1, wherein a leading edge of the contact surface has an inclined profile to follow a contour of the glans.

7. Apparatus according to claim 1 further comprising:—a second outwardly directed contact portion for applying stimulation to a female's genitalia.

8. Apparatus according to claim 7, wherein the second outwardly directed contact portion has a contact surface having undulating configurations.

9. Apparatus according to claim 1, wherein the side portions comprise opposed recessed portions for affording a holding area for a user of the apparatus.

10. A method of tolerizing a penis by stimulation for delaying a latency period to ejaculation, the method comprising the steps: a) utilizing the apparatus of claim 1 on a regular basis, by stroking the apparatus either manually or through aforementioned a vibrator or excitation means against a base of a glans and/or adjacent area up to a point of feeling an urge to ejaculation; b) discontinuing the stroking for a pause; and c) restarting stroking again; wherein the method is repeated for up to 30 minutes.

11. A method according to claim 10, wherein the apparatus is used for a period of 6 weeks, at least once per week for up to 30 minutes.

12. A method according to claim 10, wherein the apparatus is used for a period of 6 weeks, 3 times weekly for up to 30 minutes.

* * * * *